United States Patent [19]

Bark

[11] Patent Number: 5,377,694
[45] Date of Patent: Jan. 3, 1995

[54] FITMENT SYSTEM FOR ATTACHING FLUID COLLECTION DEVICES TO SURGICAL DRAPES

[75] Inventor: Jeffrey E. Bark, Green Bay, Wis.

[73] Assignee: Little Rapids Corporation, Green Bay, Wis.

[21] Appl. No.: 174,229

[22] Filed: Dec. 28, 1993

[51] Int. Cl.⁶ .............. A61B 19/00; A61B 19/08; A61F 5/44
[52] U.S. Cl. .............. 128/849; 604/350; 128/853
[58] Field of Search .............. 128/849–856; 604/347, 14 355

[56] References Cited

U.S. PATENT DOCUMENTS

| | | |
|---|---|---|
| D. 263,078 | 2/1982 | Eddelman . |
| D. 270,947 | 11/1983 | Mehra et al. . |
| D. 285,487 | 9/1986 | Tjernagel . |
| 2,777,490 | 1/1957 | Munk ............... 150/8 |
| 3,419,227 | 12/1968 | Werkmeister ............... 403/350 |
| 3,683,914 | 8/1972 | Crowley . |
| 4,137,573 | 2/1979 | Kroeger . |
| 4,228,550 | 10/1980 | Salkind . |
| 4,266,300 | 5/1981 | Partridge . |
| 4,490,144 | 12/1984 | Steigerwald ............... 604/350 |
| 4,685,472 | 8/1987 | Muto . |
| 4,738,673 | 4/1988 | Shepard . |
| 4,799,928 | 1/1989 | Crowley . |
| 4,828,554 | 5/1989 | Griffin ............... 604/350 |
| 4,902,421 | 2/1990 | Pascale et al. . |
| 4,974,604 | 12/1990 | Morris ............... 128/853 |
| 4,986,822 | 1/1991 | Anderson ............... 604/355 |
| 4,997,435 | 3/1991 | Demeter . |
| 5,002,541 | 3/1991 | Conkling et al. . |
| 5,014,686 | 5/1991 | Schafer . |
| 5,069,878 | 12/1991 | Ehrenkranz . |
| 5,174,306 | 12/1992 | Marshall ............... 128/849 |
| 5,318,551 | 6/1994 | Di Cristo ............... 604/349 |

OTHER PUBLICATIONS

"3 And 25mm Syringe Filters", The Filtertek Companies.

Primary Examiner—Michael A. Brown
Attorney, Agent, or Firm—Niro, Scavone, Haller & Niro

[57] ABSTRACT

This invention relates to fitment systems designed to connect filters, collection pouches and drains to surgical drapes used in high-fluid procedures. The preferred embodiment provides a ring-and-groove fluid-tight seal and a large fitment bore that can accommodate passage of kidney stones, bone and tissue fragments and the like along with blood, urine or irrigation fluid. Sealing is accomplished by the interaction of a slightly oversize ring with a slightly undersize groove around the bore of the fitment.

9 Claims, 1 Drawing Sheet

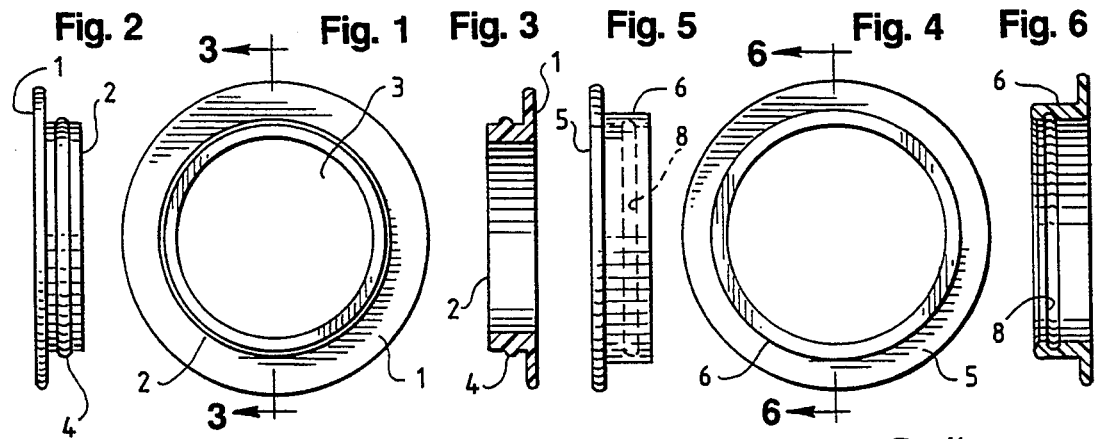
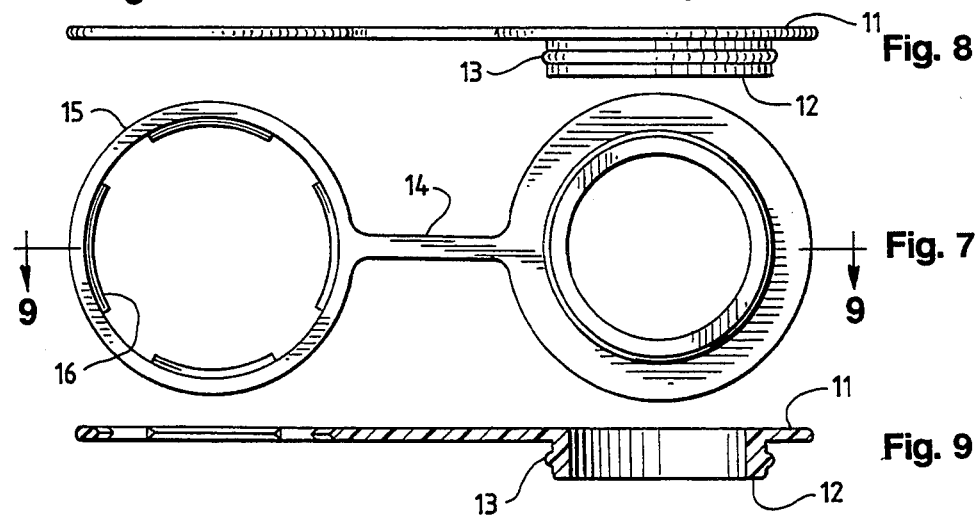
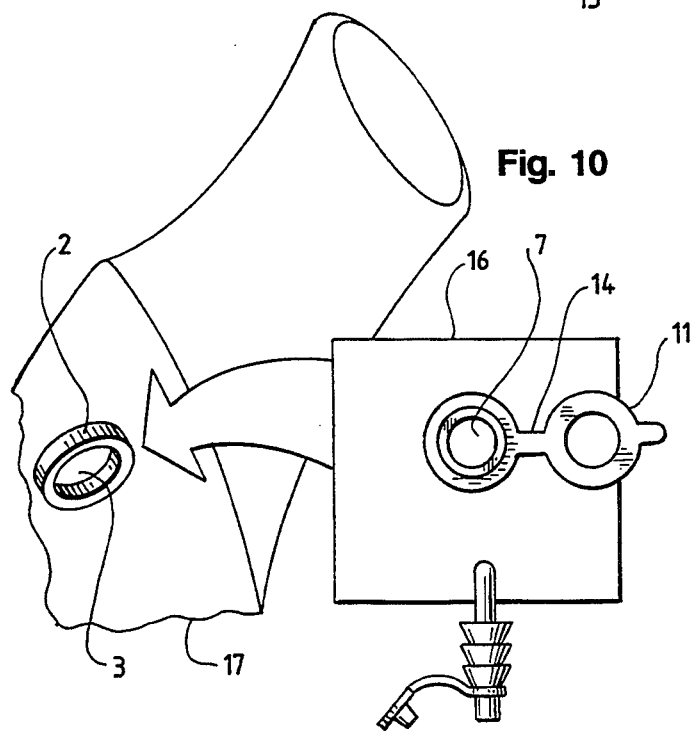

FITMENT SYSTEM FOR ATTACHING FLUID COLLECTION DEVICES TO SURGICAL DRAPES

BACKGROUND OF THE INVENTION

1. Field of the Invention

A variety of surgical procedures such as extracorporeal shock wave lithotripsy (ESWL) for removal of kidney stones and transurethral prostatectomies require collection and/or filtration of body fluids such as blood, urine and irrigation fluids (both during and after the surgical procedure itself), and in some instances collection of entrained solid materials (for example, broken stones or body tissue) for subsequent laboratory analysis. It is sometimes desired to collect the solid materials quantitatively, to allow a determination of their total mass to be made. In virtually all cases it is desirable to reduce or eliminate handling of body fluids and collected samples by hospital personnel, in order to minimize the risk of sample loss and exposure of hospital personnel to contaminants such as the AIDS virus.

My invention relates to fitment systems designed to connect filters, collection pouches and drains to surgical drapes used in high-fluid procedures. My preferred embodiment provides a ring-and-groove fluid-tight seal and a large fitment bore that can accommodate passage of kidney stones, bone and tissue fragments and the like along with blood, urine or irrigation fluid.

2. Description of the Prior Art

U.S. Pat. No. 4,529,102 (Quinn, et al) discloses an enteric feeding bag having a permanently attached valve to which a plug is attached by means of a flexible strap. The plug fits inside the throat of the valve by friction. Quinn cites U.S. Pat. No. 2,777,480 (Munk) as an example of a suitable closure device. Munk discloses a closure element suitable for flexible plastic devises such as toy wading pools. The closure element uses a flexible strap to attach a cup-shaped plug. Sealing is effected by friction, and the internal pressure of water helps tighten the seal.

In U.S. Pat. No. 4,754,895 (Lardner, et al), a screw-type closure uses a partially circular protrusion to engage a lumen. The device is said to be usable for drain closures on plastic bag-type containers.

U.S. Pat. No. 4,731,978 (Martensson) discloses a flexible bag having a separate inlet member and a closing member designed for closing the inlet member from the inside of the bag. The inlet and closing members are stiffer than the bag and are substantially resistant to deformation. The closing member fits inside the throat of the inlet member. The exterior cylindrical surface of the closing member is fitted with annular protuberances or ridges which fit the inside surface of the sleeve, forming a series of seals.

U.S. Pat. No. 4,618,994 (Bishop) shows a closure device for a urostomy bag. FIG. 1 illustrates the device in its opened condition. Closure is accomplished by depressing a male member into the top of a drainage tube, where the bulging sides of the male member effect a seal. An additional cap, which also works by friction, can be inserted into the bottom end of the sleeve to provide an additional seal.

FIG. 10 of U.S. Pat. No. 4,974,604 (Morris) illustrates an arrangement used to attach an outlet fitting 153 to a fluid collection system for a surgical drape. Two hollow fittings and a compressible foam washer are involved. Closure is by means of frictional or force fit.

Thus, prior art devices emphasize screw and friction closures. None provides the advantages of a large-bore, snap closure suitable for use on surgical drapes and filters and based upon an oversize ring/undersize groove arrangement that provides a dual fluid seal.

SUMMARY OF THE INVENTION

My invention provides a large-bore snap closure especially suitable for attaching filters, large drain tubes and fluid collection pouches to surgical drapes used in high-fluid procedures. In the embodiment for use with a flexible filter pouch, this invention comprises (1) a large-bore pouch fitment, which is a circular plastic collar suitable for permanent attachment to a collection pouch and having a circular groove cut or formed within the throat of the fitment; (2) a large-bore drape fitment suitable for permanent attachment to a surgical drape and having a raised circular ring on the exterior of the fitment suitable for mating with the circular groove inside the throat of the drape fitment; and (3) a plug similar in configuration to the drape fitment except that it is blocked off to form a solid cap suitable for closing and sealing the collection pouch after use. The cross-sectional radius of the circular ring is slightly larger than the cross-sectional radius of the groove, thus providing a dual line seal. The oversize ring snaps into the groove in a manner perceptible by touch. The pouch fitment further comprises a flange which prevents insertion of the drape fitment on the plug past the point of engagement of the ring and groove.

In a preferred embodiment of my invention, the plug further comprises a circular collar suitable for engagement around the pouch fitment, to which the fitment plug is attached by means of a flexible strap. When it is desired to close the pouch, the plug is inserted into the pouch fitment, causing the strap to be folded over. The collar is retained on the pouch fitment before use by means of a plurality of slightly raised tabs in the throat of the collar.

BRIEF DESCRIPTION OF THE DRAWINGS

FIG. 1 is a top view of the surgical drape fitment of my invention.

FIG. 2 is a side view of the surgical drape fitment.

FIG. 3 is a cross-sectional view of the surgical drape fitment.

FIG. 4 is a top view of the pouch fitment.

FIG. 5 is a side view of the pouch fitment.

FIG. 6 is a cross-section view of the pouch fitment.

FIG. 7 is a top view of the plug.

FIG. 8 is a side view of the plug.

FIG. 9 is a cross-sectional view of the plug.

FIG. 10 shows the fitment system of my invention installed on a surgical drape and a filter pouch.

FIG. 11 is a partial cross-sectional view of the drape fitment and pouch fitment in mating engagement, illustrating the creation of dual sealing surfaces by the resilient materials of the fitments.

DETAILED DESCRIPTION OF MY PREFERRED EMBODIMENT

Referring first to the surgical drape fitment portion of my invention, FIGS. 1–3 show a circular drape fitment comprising a drape attachment flange 1 and a raised male cylindrical element 2 having a large-bore central aperture 3 of sufficient internal diameter to accommodate blood, urine or other fluids encountered during surgical procedures and pieces of bone, tissue and the like that may be encountered in the fluid. The drape attachment flange is used to permanently affix the drape fitment to a surgical drape using any of a variety of means known in the art, such as adhesives, heat sealing, RF sealing and the like. The exterior cylindrical surface of raised male cylindrical element 2 is encircled by a sealing ring 4 having a semi-circular cross-section, as shown in FIG. 11.

FIGS. 4–6 illustrate the mating pouch fitment. It comprises a pouch attachment flange 5 and a raised female cylindrical element 6 having a large-bore central aperture 7 that is concentric with the aperture 3 of the drape fitment, and communicates with that aperture. The interior of raised female cylindrical element 6 is encircled by a groove 8 that mates with the sealing ring 4 of the drape fitment.

In my preferred embodiment, the exterior diameter of raised male cylindrical element 2 is about 1.502 inches. The raised female cylindrical element 6 has an internal diameter of about 1.500 inches, two thousandths of an inch smaller than the external diameter of raised male cylindrical element 2. Thus, the raised male cylindrical element fits into the raised female cylindrical element tightly, by deforming the resilient plastic of which the elements are fabricated. Suitable materials of construction for the fitments include low density polyethylene (LDPE); high density polyethylene (HDPE); polypropylene, polyvinyl chloride; EVA or blends of thermoplastic materials. Thermoset materials such as silicone elastomer or polyurethane also may be used.

In cross-section, as shown in FIG. 11, the radius of the sealing ring 4 exceeds the radius of the groove 8. (In the preferred embodiment the radius of the sealing ring cross-section is about 0.078 inches and the radius of the groove cross-section is about 0.031 inches. Preferably, the radius of the groove should be less than one half of the radius of the ring.) This provides two points of contact between the ring and the groove, at points 9 and 10 shown in FIG. 11. The result is a liquid seal that is superior to the surface seal that would result if the two radii were the same.

As a result of the combination of slightly oversizing both the raised male member and the sealing ring, the pouch and drape fitments fit together with a perceptible "click" that indicates to the user that a fluid-tight connection has been made.

FIGS. 7–9 illustrate the mating plug fitment and its retaining collar and strap. The plug fitment comprises a base flange 11 having a raised male cylindrical element 12. A sealing ring 13 encircles the raised male cylindrical element 12. The dimensions of the raised male cylindrical element 12 and the sealing ring 13 are substantially the same as the corresponding structures 2 and 4 of the drape fitment, except that the raised cylindrical element 12 of the plug fitment does not have any aperture, since it serves as a cap.

In the preferred embodiment, the vertical spacing between the base flange 11 and the sealing ring 13 of the plug is such that the male raised cylindrical element 12 of the plug cannot be forced into the female raised cylindrical element 6 of the pouch fitment past the distance required for engagement of sealing ring 13 and groove 8. The same is true of the vertical spacing between flange 1 and sealing ring 4 of the drape fitment. This likewise makes it impossible to force the drape fitment too far into the pouch fitment.

In the preferred embodiment of my invention, the plug fitment further comprises retaining strap 14 and retaining ring 15. The retaining ring incorporates a plurality of ridges 16 on its inner circumference. In use, retaining ring 15 encircles raised female cylindrical element 6 of the pouch fitment. Ridges 16 assist in holding ring 15 onto the pouch fitment as shown in FIG. 11.

In use, filter or collection pouch 16 is packed together with a high-fluid surgical drape 17, but with the fitments disassembled. Before or during the surgical procedure, the drape fitment is snapped into the pouch fitment, providing a sanitary and fluid-tight attachment. This is accomplished by the dual resilient seals affected at points 9 and 10 on the peripheries of the mating rings and groove, as shown in FIG. 11. After the surgical procedure is complete, the pouch is detached and the plug is snapped into the pouch fitment, sealing its contents for disposal or transport to a laboratory.

The foregoing specific embodiment is intended to illustrate the possible applications of our invention. It will be apparent to those of ordinary skill in the art that many changes and modifications could be made while remaining within the scope of the invention. For example, the fitment system of my invention could be made in a variety of bore diameters. It could be used for attaching large-bore drain hoses to surgical drapes, since it is not limited to attaching fluid filtration or collection pouches. It could be used simply as a closure for a pouch or other fluid-containing device, in which case only the pouch fitment and the plug fitment would be employed. Indeed, it is usable for making fluid-tight connections between a wide variety of flexible or rigid fluid-containing devices, although it is especially suitable for use with flexible plastic drapes and pouches.

It is my intention, therefore, to cover all such equivalent structures and to limit my invention only as specifically delineated in the following claims.

I claim:

1. A fluid-tight fitment system for releasably attaching a first fluid-containing device to a second fluid-containing device, comprising:
   a. a drape fitment having a drape attachment flange suitable for permanent attachment to a first fluid-containing device:
   b. a raised male cylindrical element formed onto said drape attachment flange and having a large bore central aperture and an exterior cylindrical surface;
   c. a sealing ring encircling said exterior cylindrical surface of said raised male cylindrical element and having a semicircular cross-section and a radius of said cross-section;
   d. a pouch fitment having a pouch attachment flange suitable for permanent attachment to a second fluid-containing device:
   e. a raised female cylindrical element formed onto said pouch attachment flange and having a large bore central aperture and an interior cylindrical surface;
   f. a groove encircling said interior cylindrical surface of said raised female cylindrical element and having a semicircular cross-section with a radius smaller than the radius of said cross-section of said sealing ring.

2. The fitment system of claim 1 wherein said radius of said groove is less than one half of said radius of said sealing ring.

3. The fitment system of claim 1, further comprising:
   a. a plug fitment having a base flange;

b. a raised male cylindrical element formed onto said base flange and having an exterior cylindrical surface;

c. a second sealing ring encircling said exterior cylindrical surface of said raised male cylindrical element and having a semicircular cross-section and a radius of said cross-section larger than said radius of said cross-section of said groove.

4. The fitment system of claim 3, wherein said radius of said second sealing ring is more than twice the radius of said groove.

5. The fitment system of claim 3, further comprising a retaining strap with a proximal end and a distal end attached to said base flange of said cap; wherein said proximal end of said retaining strap terminates in a retaining ring suitable for releasable attachment to said raised female cylindrical element formed on said pouch attachment flange.

6. A fluid-tight closure system for a fluid-containing device, comprising:

a. a pouch fitment having a pouch attachment flange suitable for permanent attachment to said fluid-containing device:

b. a raised female cylindrical element formed onto said pouch attachment flange and having a large bore central aperture and an interior cylindrical surface;

c. a groove encircling said interior cylindrical surface of said raised female cylindrical element and having a semicircular cross-section with a radius;

d. a plug fitment having a base flange;

e. a raised male cylindrical element formed onto said base flange and having an exterior cylindrical surface;

f. a second sealing ring encircling said exterior cylindrical surface of said raised male cylindrical element and having a semicircular cross-section and a radius of said cross-section larger than said radius of said cross-section of said groove.

7. A fluid-tight fitment system for releasably attaching a surgical drape to a pouch, comprising:

a. a drape fitment having a drape attachment flange suitable for permanent attachment to a surgical drape:

b. a raised male cylindrical element formed onto said drape attachment flange and having a large bore central aperture and an exterior cylindrical surface;

c. a sealing ring encircling said exterior cylindrical surface of said raised male cylindrical element and having a semicircular cross-section and a radius of said cross-section;

d. a pouch fitment having a pouch attachment flange suitable for permanent attachment to a pouch:

e. a raised female cylindrical element formed onto said pouch attachment flange and having a large bore central aperture and an interior cylindrical surface;

f. a groove encircling said interior cylindrical surface of said raised female cylindrical element and having a semicircular cross-section with a radius smaller than the radius of said cross-section of said sealing ring.

8. The fitment system of claim 7, further comprising:

a. a plug fitment having a base flange;

b. a raised male cylindrical element formed onto said base flange and having an exterior cylindrical surface;

c. a second sealing ring encircling said exterior cylindrical surface of said raised male cylindrical element and having a semicircular cross-section and a radius of said cross-section slightly larger than said radius of said cross-section of said groove.

9. The fitment system of claim 8, further comprising a retaining strap with a proximal end and a distal end attached to said base flange of said cap; wherein said proximal end of said retaining strap terminates in a retaining ring suitable for releasable attachment to said raised female cylindrical element formed on said pouch attachment flange.

* * * * *